United States Patent [19]

Le et al.

[11] Patent Number: 5,011,479
[45] Date of Patent: Apr. 30, 1991

[54] COVER AND CONNECTOR FOR HYPODERMIC NEEDLE

[76] Inventors: Son Le, 372 Christopher Dr., San Francisco, Calif. 94131; Phillip Yang, 1557 Midvale Ave., Los Angeles, Calif. 90024

[21] Appl. No.: 523,298

[22] Filed: May 14, 1990

Related U.S. Application Data

[63] Continuation of Ser. No. 418,270, Oct. 6, 1989, abandoned, and a continuation-in-part of Ser. No. 360,261, Jun. 2, 1989, abandoned.

[51] Int. Cl.$^5$ .............................................. A61M 5/32
[52] U.S. Cl. ..................................... 604/198; 604/263
[58] Field of Search ............... 604/198, 263, 187, 192, 604/110

[56] References Cited

U.S. PATENT DOCUMENTS

| | | |
|---|---|---|
| 4,592,744 | 6/1986 | Jagger et al. . |
| 4,596,562 | 6/1986 | Vernon . |
| 4,610,667 | 9/1986 | Pedicano et al. . |
| 4,623,336 | 11/1986 | Pedicano et al. . |
| 4,629,453 | 12/1986 | Cooper . |
| 4,643,722 | 2/1987 | Smith Jr. . |
| 4,654,034 | 3/1987 | Master et al. . |
| 4,659,330 | 4/1987 | Nelson et al. . |
| 4,664,259 | 5/1987 | Landis . |
| 4,695,274 | 9/1987 | Fox ........................................ 604/198 |
| 4,717,386 | 1/1988 | Simmons . |
| 4,720,285 | 1/1988 | Pickhard . |
| 4,725,267 | 2/1988 | Vaillancourt . |
| 4,731,059 | 3/1988 | Wanderer et al. . |
| 4,735,617 | 4/1988 | Nelson et al. . |
| 4,735,618 | 4/1988 | Hagen . |
| 4,737,149 | 4/1988 | Gillilan . |
| 4,740,204 | 4/1988 | Masters et al. . |
| 4,740,205 | 4/1988 | Seltzer et al. . |
| 4,743,233 | 5/1988 | Schneider . |
| 4,747,835 | 5/1988 | Sandhaus . |
| 4,767,412 | 8/1988 | Hymanson . |
| 4,775,367 | 10/1988 | Schmidt . |
| 4,781,697 | 11/1988 | Slaughter . |
| 4,819,659 | 4/1989 | Sitar ................................ 605/198 X |
| 4,820,277 | 4/1989 | Norelli . |
| 4,832,696 | 5/1989 | Luther et al. ................... 604/198 X |

OTHER PUBLICATIONS

Jagger, M. P. H., PH.D., et al., Rates of Needle-Stick Injury Caused by Various Devices in a University Hospital, Aug. 4, 1988, pp. 284-288, vol. 319.

Primary Examiner—John D. Yasko
Attorney, Agent, or Firm—Poms, Smith, Lande & Rose

[57] ABSTRACT

A needle connecting apparatus for connecting a needle to a syringe and for covering the needle for disposal includes a connector housing. A first mounting point on the connector housing mounts the housing to a syringe body. A second mounting point on the connector housing mounts base of a needle to the housing. A rigid needle cover is movably mounted to the connector housing for exposing a needle mounted to the connector housing when in a first position and for covering a needle mounted to the connector housing when in a second position.

13 Claims, 6 Drawing Sheets

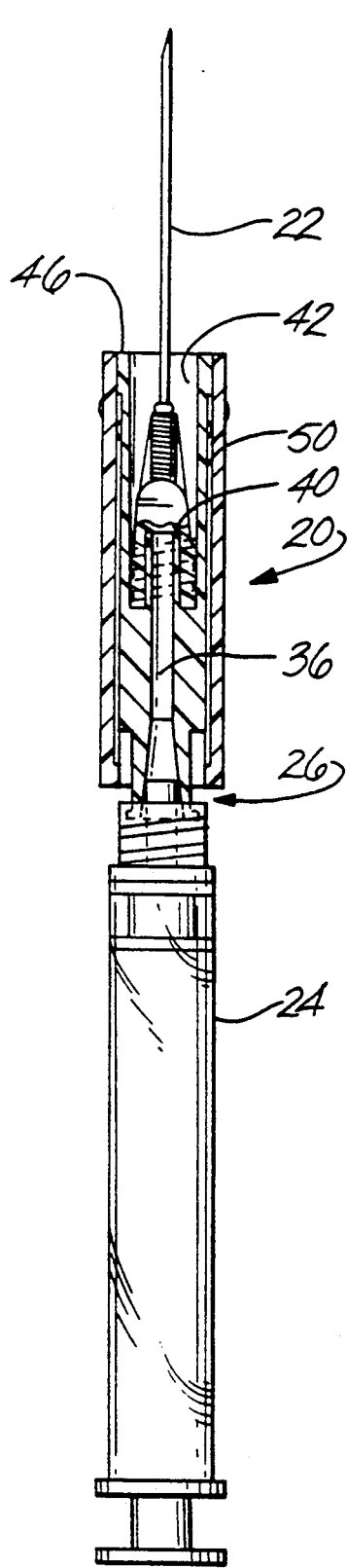
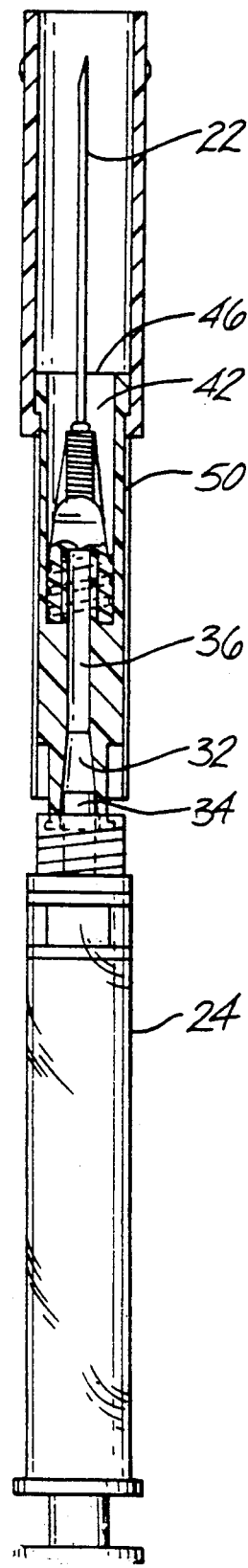
Fig. 1
Fig. 2

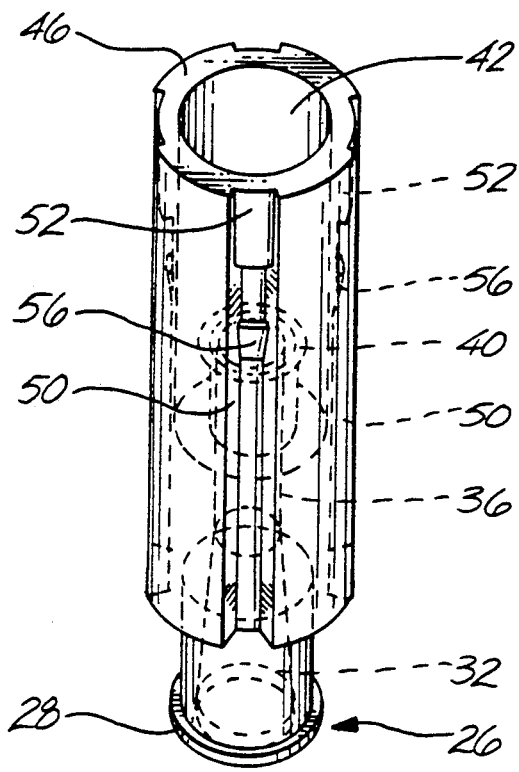
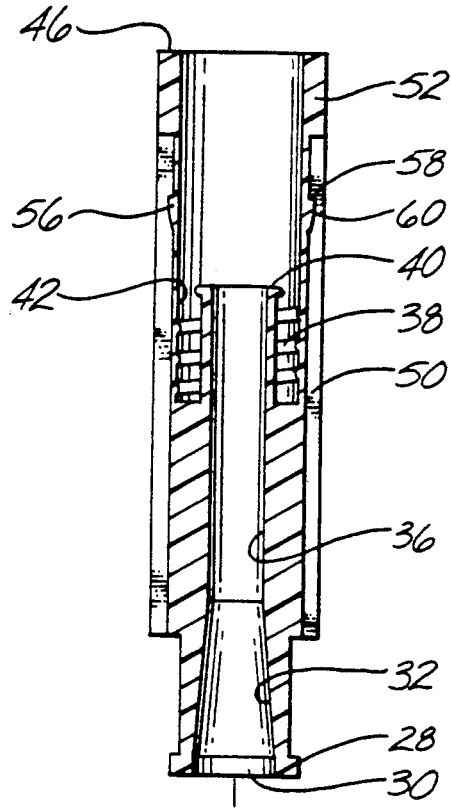
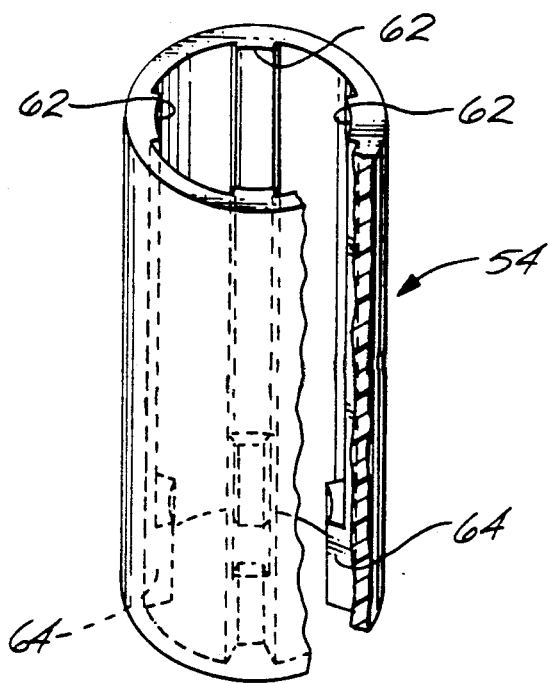
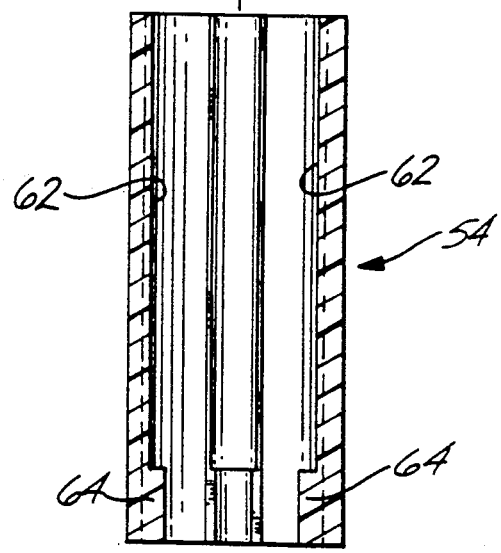

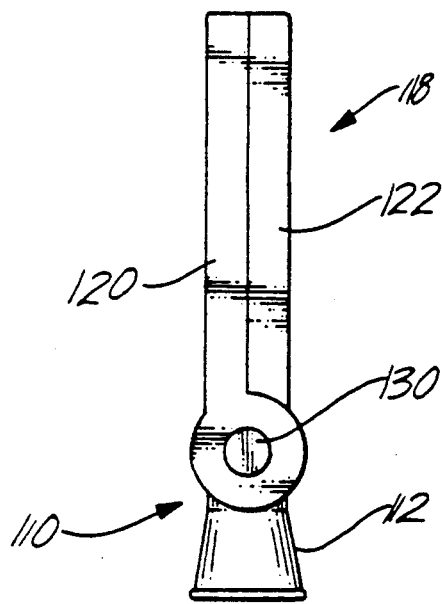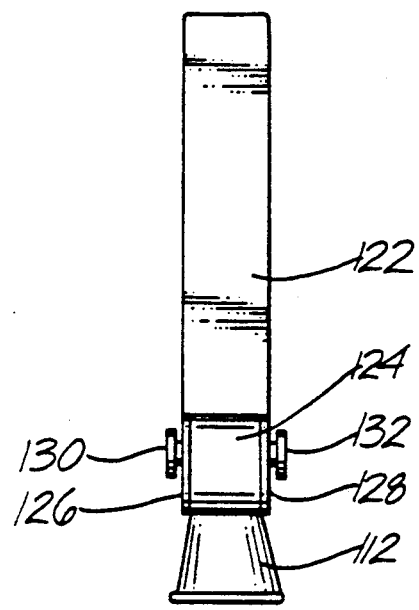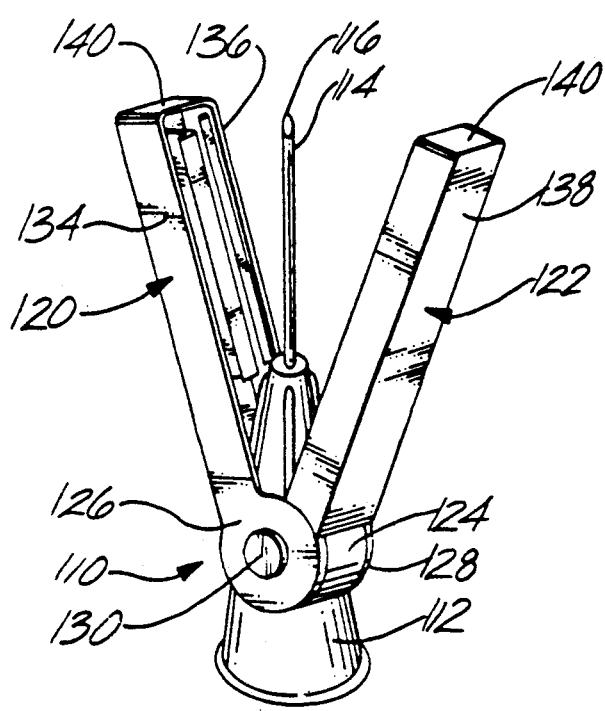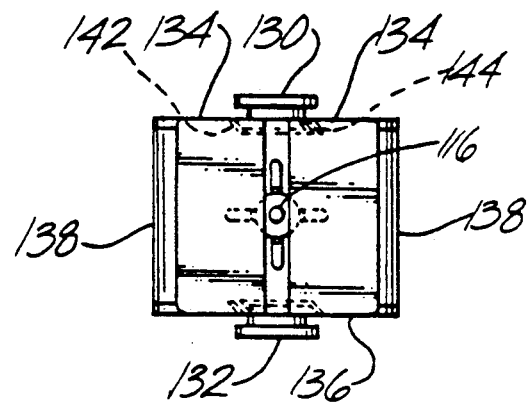

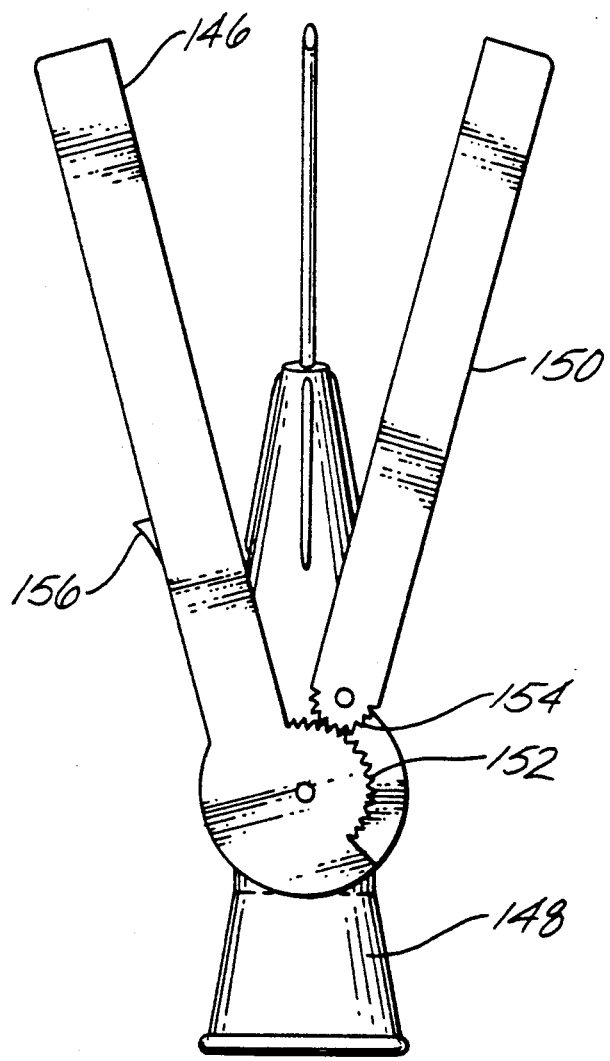
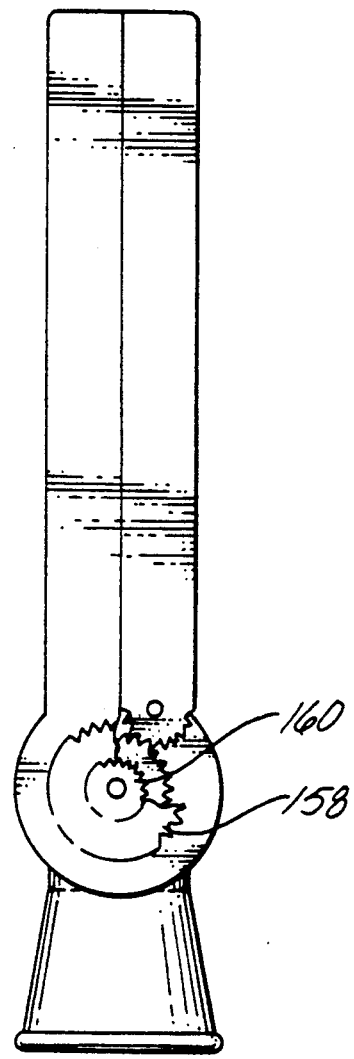

COVER AND CONNECTOR FOR HYPODERMIC NEEDLE

This application is a continuation of application Ser. No. 07/418,270, filed Oct. 6, 1989, now abandoned, which was a continuation-in-part of application Ser. No. 360,261, filed June 2, 1989, now abandoned.

BACKGROUND OF THE INVENTION

1. Field Of The Invention

The present invention relates to protective covers for hypodermic needles and, more specifically, to connecting apparatus for connecting a needle to a syringe and for covering the needle for disposal.

2. Related Art

Disposable hypodermic needles typically available cover the needle with a plastic removable cap. The cap protects the needle and medical personnel and users from injury due to accidental needle stick. The cap covers the needle from its tip to its base. The plastic cap is primarily intended to protect the needle before use and to protect personnel after use prior to complete disposal of the needle. Other needle protection designs may incorporate a flexible rubber cover for use with evacuated vials, etc.

Hard plastic is a preferred cover material but a removable cap creates a possibility of needle stick injury. Needle sticks may occur when personnel fail to properly join the cap and the needle, resulting in needle stick of the hand holding the cap because the hand or fingers are inadvertently allowed to come too close to the needle tip. Needle stick may also occur when the needle pierces through the cap because of misalignment during recapping or when the cap falls off of a recapped needle. Needle stick with a contaminated needle may result, for example, in illness from hepatitis or AIDS.

There is a need for a disposable hypodermic needle cover which can protect the needle prior to its use, and which can protect personnel after use of the needle from needle stick injuries such as occur when a cap is not properly replaced on the needle or when the cap falls off. There is a need for a needle cover which allows exposure or recovering of the needle without requiring the user to place a hand or finger near the tip of the needle. There is also a need for a needle cover which can be manipulated near the base of the needle to cover or uncover the needle rather than at the tip of the needle.

There is also a need for a connecting and covering apparatus with a needle cover for use with presently available needles having removable plastic caps which can be connected to a syringe whereby the presently available needle is mounted to the connecting apparatus so that the needle cover is substituted for the removable plastic cap.

SUMMARY OF THE INVENTION

A needle connecting apparatus for connecting a needle to a syringe and for covering the needle for disposal is provided which minimizes the possibility of needle stick injury by incomplete recapping of a needle or by inadvertent loss of the cap from the needle and which can accommodate presently available needles. Such a needle connecting apparatus includes a connector housing and first mounting means on the connector housing for mounting the housing to a syringe body. The connector housing includes second mounting means for mounting a base of needle to the housing. A rigid needle cover is movably mounted to the connector housing for exposing a needle mounted to the connector housing when in a first position and for covering a needle mounted to the connector housing when in a second position. The cover preferably includes a one way lock so that the cover cannot be moved again to expose the needle once the needle has been used and the cover moved into place in the second position over the needle. The needle preferably is not removable from the connector once the cover has been locked in place. In a preferred embodiment, the needle cover may be telescopically moveable relative to the connector housing so that an end of the cover extends beyond the end of the needle. In another preferred embodiment, the needle cover may include first and second rigid portions pivotally fixed to the connector housing for covering the needle when in a mutually adjacent position and which can be pivoted away from each other by grasping at least one of the first and second portions near the connector housing and pivoting it away from the needle. In a still further preferred embodiment, the two halves may interengage through gears at the base of the needle so that movement of one half will result in movement of the other half. This facilitates one-handed operation for exposing or covering the needle.

The invention will be further understood upon consideration of the drawings and the detailed description of the preferred embodiments.

BRIEF DESCRIPTION OF THE DRAWINGS

FIG. 1 is a side elevation and longitudinal section of a needle connecting and covering apparatus according to one embodiment of the present invention mounted to a syringe and with a needle attached.

FIG. 2 is a side elevation and longitudinal section of the needle connecting and covering apparatus of FIG. 1 with the needle cover in an extended position.

FIG. 3 shows a top perspective view of the needle connecting apparatus of FIG. 1 with the needle cover removed.

FIG. 4 shows a top perspective and partial cut-away view of the needle cover for use with the connecting apparatus of FIG. 3.

FIG. 5 is a side elevation and longitudinal sectional view of the needle connecting and covering apparatus of FIG. 1 with the needle cover separated from the apparatus.

FIG. 8 is a side elevational view of one embodiment of a hypodermic needle and protective cover assembly showing the protective cover in a fully closed configuration.

FIG. 9 is a frontal elevational view of the needle and protective cover of FIG. 8.

FIG. 10 is a perspective view of the needle and cover assembly of FIG. 8 with the cover partially open to expose the needle.

FIG. 11 is a top plan view of the needle and protective cover assembly of FIG. 8 showing the cover partially open and unlocked.

FIG. 14 is a side elevation view of a further embodiment of the needle and cover assembly.

FIG. 15 is a side elevation view of a still further embodiment of the needle and cover assembly.

DETAILED DESCRIPTION OF THE PREFERRED EMBODIMENTS

Figure 6:
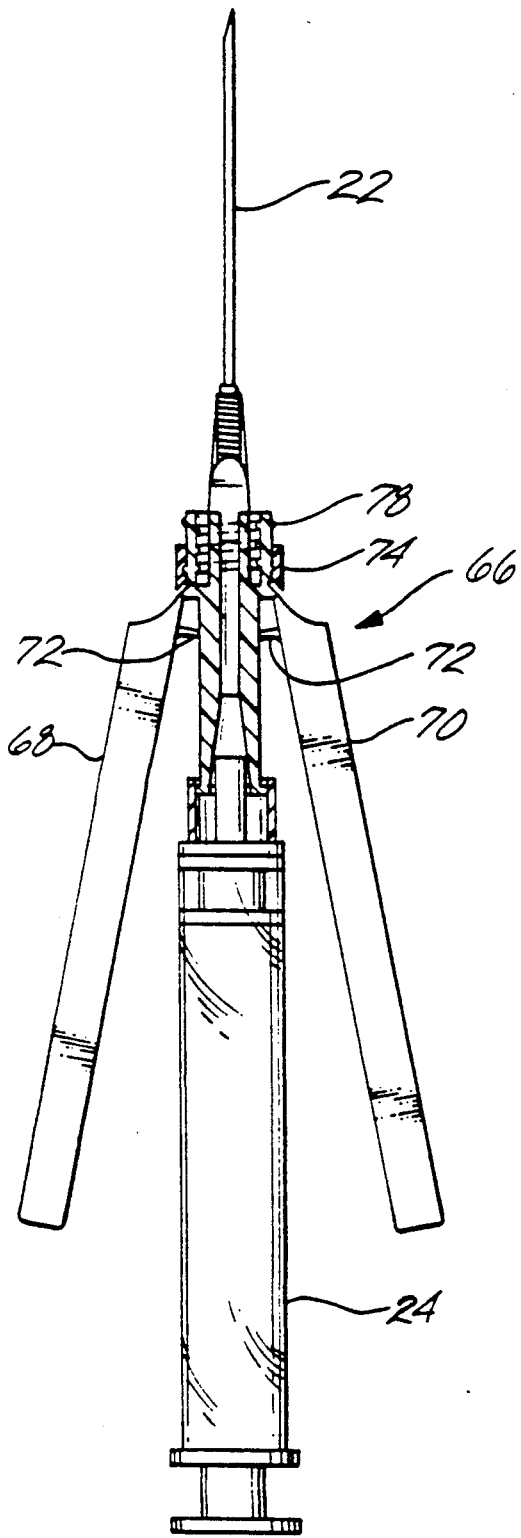
FIG. 6 is a side elevation and longitudinal sectional view of a needle connecting and covering apparatus according to a further embodiment of the present invention.

A needle connecting and covering apparatus for connecting a needle to a syringe and for covering the needle for disposal is described which minimizes the possibility of needle stick injury resulting from failure to properly mate the needle and cover or from inadvertent removal of the cap from the needle, but which can still accommodate presently available needles which use a removable cap. The disclosed combination also provides for covering and uncovering the needle by operating the cover from a location adjacent the base of the needle. In one preferred embodiment, a needle connecting and covering apparatus 20 (FIGS. 1-5) connects a hypodermic needle 22 to a syringe 24. The connector provides means by which presently available hypodermic needles with removable caps can be coupled to syringes whereby the cover on the connector replaces the removable cap which comes with the needle. The cover allows exposure and recovering of the needle without the user having to place a hand or finger near the tip of the needle. The cover can be moved into place to cover the needle by manipulating the cover near the base of the needle.

One end 26 of the connector includes radially extending flanges 28 for threadably engaging internal threads formed at the end of the barrel of the syringe. The flanges 28 are formed at the rim of the end of the connector which defines a central opening 30 which leads into a converging passageway 32 in the interior of the connector. The converging passageway 32 fits over the cylindrical tip 34 on the end of the syringe. Threading of the connector onto the end of the syringe causes frictional engagement of the cylindrical tip with the inside surface of the passage 32 in a manner similar to the engagement which occurs with presently available needles when mounted on the end of the syringe.

The converging passageway leads into a central longitudinally extending flow passage 36 formed in, or bored through, the connector and through a longitudinally extending tube 38 terminating at a tube end 40, seen most clearly in FIGS. 3 and 5.

The longitudinally extending tube extends upwardly from the bottom of a bore 42 a sufficient distance so that a base 44 of the needle 22 can fit over and enclose the tube end 40 and form a frictional engagement. The bore 42 is defined by a cylindrical wall extending from a second end 46 of the connector down to the bottom of the bore from which the tube 38 extends upwardly. The portion of the cylindrical wall of the bore surrounding the tube 38 includes internal threads 48 for threadably engaging the base of the hypodermic needle. The length of the wall from the internal threads 48 to the second end 46 will be selected based on the lengths of the needles used with the syringe and the particular type of needle cover on the connector.

In a first preferred embodiment of a needle connector having a telescoping needle cover, the outside surface of the connector is preferably cylindrical and preferably extends from a point adjacent the converging passage 32 to the second end 46 of the connector. The outside surface includes preferably four longitudinally extending grooves 50 extending substantially the length of the outer wall. Each groove has a block 52 at the end for preventing further longitudinal movement of a telescoping needle cover 54. Each block extends from the bottom of the respective groove only part way to the top of the groove. Each groove also includes, spaced longitudinally from a respective block 52, a one-way locking boss 56 extending from the bottom of the groove part way to the top of the groove. Each boss 56 includes a radial surface extending from the base of the groove to the outer most point on the boss. The boss further includes a curved surface 60 extending from the top most point on the boss away from the radial surface 58 back down to the bottom of the groove (FIG. 5). There is sufficient space between the block 52 and radial surface on the locking boss 56 to accommodate a locking ridge on the telescoping needle cover 54.

The needle cover 54 (FIGS. 4 and 5) is preferably a substantially hollow cylinder with a substantially uniform external surface and four lands 62 on the internal surface. The lands engage corresponding grooves 50 on the external surface of the connector so that the needle cover can slide longitudinally relative to the connector. Each land extends inwardly from the interior surface of the needle cover a distance sufficient to engage the respective groove, but preferably does not extend to the bottom of the groove. At the bottom of the cylinder, each land has a locking ridge 64 for riding up over the slopping surface 60 on the respective locking boss and then fitting into the space between a locking boss and the respective block 52 in the groove. Engagement of the locking ridge with each respective boss serves as a one-way lock covering the needle and preventing the needle from being exposed again after use.

As can be seen in FIG. 5, the blocks 52 at the top of each groove do not extend to the top of the groove, thereby allowing the respective land to be guided in the groove over the block 52. The block 52 prevents the telescoping needle cover from coming off the end of the connector when the locking ridge hits the lower end of the block. The radially extending surface 58 on the boss 56 locks the needle cover in place once the locking ridge 64 falls into place between the boss and the block 52.

In operation, the needle connecting and cover apparatus is mounted on the end of a syringe by threading the first end over the tip of the syringe. The ridged telescoping cover may already be installed on a connector and packaged together so that the cover is in a first position such as is shown in FIG. 1. A needle is then threaded into the internal threads 48 of the bore and the removable cap discarded when the syringe and needle combination are ready to be used. After use, the telescoping cover 54 is moved along the connector and locked into place in a second position shown in FIG. 2 and the apparatus discarded.

The apparatus is preferably formed or molded from a suitable plastic. The needle cover is rigid so that it cannot become exposed once the cover is locked in place. The four grooves in the connector are used to guide the cover and also prevent any substantial rocking of the cover back and forth on the connector. The cover and connector can be made long enough to cover almost all commonly used needles. The apparatus still allows adequate access for the needle when the cover is retracted.

In an alternative embodiment of the connector and cover (FIGS. 6 and 7), the outer wall of the connector extends only as far as the tube end extending from the bottom of the bore. The rigid needle cover 66 includes left and right halves 68 and 70, respectively, which pivot around respective pivot points on the outer surface of the connector. The left and right halves may be locked into an open position by respective plastic stays 72 connecting each half to the connector. This prevents the left and right halves from moving around until the stays are broken to cover the needle.

Figure 7A:
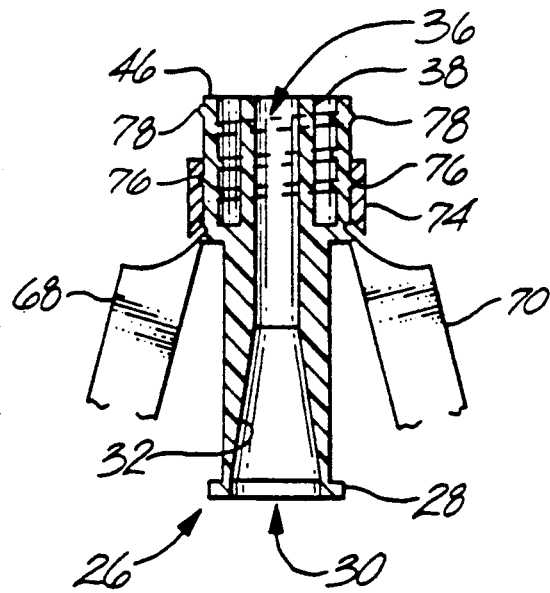
FIGS. 7 and 7b are detailed views of part of the needle connecting and covering apparatus of FIG. 6.
Figure 7B:
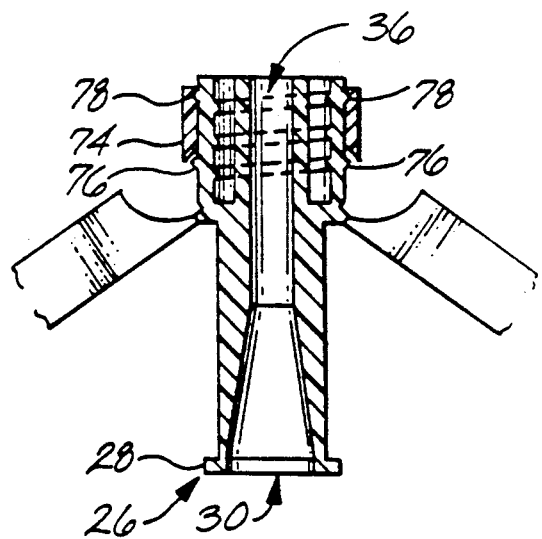

A further stay may be provided in addition to or as an alternative to the stays 72 to prevent movement of the needle cover until the needle is to be covered. A ring or slide 74 encircles the outside surface of the connector. The slide is held in place by suitable detentes 76 so that an inwardly extending surface at the lower end of the slide covers and bears against respective surfaces on the left and right halves of the needle cover, thereby preventing the left and right halves from moving. When the slide is moved longitudinally to the end of the connector and locked in place by second detents 78, the left and right halves of the needle cover are free to move (FIG. 7b). In the preferred embodiment, the left and right halves are pivotable relative to the connector by means of a suitable plastic connection which allows rotation of the left and right halves relative to the connector but provides sufficient strength to prevent the needle cover from being removed from the connector.

As with the telescoping needle cover, the left and right halves are rigid to substantially prevent the needle from puncturing the needle cover and so that the needle cover can be manipulated from a point adjacent the base of the needle. A one directional lock is also preferably included so that the needle cannot be exposed again after it has been covered up. The locking mechanism for the embodiment of the needle cover shown in FIGS. 6 and 7 is described more fully below.

As a further embodiment of a needle cover which may be used with the connector described above or alone a protective cover combination will be described which minimizes the possibility of needle stick injury resulting from failure to properly mate the needle and cover or from inadvertent removal of the cap from the needle. The disclosed combination also provides for covering and uncovering the needle by operating the cover from a location adjacent the base of the needle. In a preferred embodiment, a needle and a cover combination 10 (FIGS. 8-10) includes a base 112 and a needle 114 supported by and mounted in the base as is well known in the art. The base can be mounted on the tip of a syringe or other device as is also well known in the art. It is to be understood that the needle can be any needle presently available, for example and without limitation, hypodermic needles, vacutainer needles, intravenous and intra-arterial needles and spinal needles. The needle extends from the base to a tip 116. The cover combination or needle cover 118 includes first and second rigid portions 120 and 122, respectively, pivotally fixed to the base for covering the needle when in a mutually adjacent position such as that shown in FIG. 8. The first and second portions can also be pivoted relative to the base away from each other to a position, such as that shown in FIG. 10, by grasping at least one of the first and second portions near the base and pivoting it away from the needle.

The base further includes a mounting portion or boss 24 approximately intermediate the ends of the base on which are pivotally mounted the first and second halves of the needle cover. The first and second halves include corresponding mounting flanges 126 and 128, respectively, for mounting each half on a corresponding flat face of the mounting boss 124 and pivoting about first and second mounting pins 130 and 132, respectively.

Each half of the needle cover includes an open rectangular box portion for surrounding a respective half of the needle and upper portion of the base. Each box portion includes a left side 134, a right side 136, a back side 138 and a top side 140. The outward shape of the first and second halves are mirror images of each other. However, in one embodiment, the top side of the first half can be longer than the top side of the second half so that, upon joining of the first and second halves, the tops of the two halves still join but the longer top side extends over the end of the needle. As can be seen in FIG. 8, the left side 134 of the second half has a flat, round-edged end adjacent the mounting flange 126 of the first half. The end of the right side of the first half is similarly curved.

It should be understood that the mounting pins 130 and 132 include rimmed heads for holding each half of the needle cover on the mounting boss 124. The space between each head and the respective mounting flange on the needle cover is exaggerated in FIG. 9 for clarity. It should also be understood that the needle covers, including the mounting flanges, the mounting boss 124 and the mounting pins are formed so as to allow pivoting of the covers about the base while still maintaining the first and second halves in alignment when they are pivoted to a mutually adjacent position about the needle.

In the embodiment of the cover shown in FIGS. 8-10, locking means such as longitudinally extending locking bars 142 and 144 (FIGS. 10 and 11) are formed on or otherwise mounted on the needle cover whereby the first and second halves may be locked together when in the mutually adjacent position. In the preferred embodiment, the locking bars form an irreversible lock for the needle cover, absent destruction of the needle cover. As shown in FIGS. 10 and 11, the first half of the needle cover includes the first locking bar 142 on the inside surface of the left side of the needle cover extending approximately from the top side 140 approximately the length of the needle. The first locking bar is formed so as to be mounted to the inside surface of the first half 120, and extending outward from the inside surface and then out of the enclosure toward the second half 122 a sufficient distance to allow engagement with the second locking bar 144. The second locking bar is on the inside surface of the second half of the needle cover. The first locking bar extends a sufficient distance out of the enclosure to allow locking of the first and second locking bars while preferably still maintaining the first and second halves of the needle cover abutting. Preferably, the locking bars are as long as the needle to insure that the first and second halves remain closed after latching.

The first locking bar preferably includes a backwardly extending edge to engage the second locking bar which is mounted on the left side of the second half and extends toward the interior of the second half. The second locking bar is preferably coextensive with the first locking bar. In the preferred embodiment, an additional pair of first and second locking bars are mounted on or formed in the opposite sides of the needle cover, but oppositely arranged relative to the first described locking bars so that the first locking bar on the second half is diagonally opposite the first locking bar on the first half, thereby providing symmetry. It should be understood that other locking mechanisms are possible.

Figure 12:
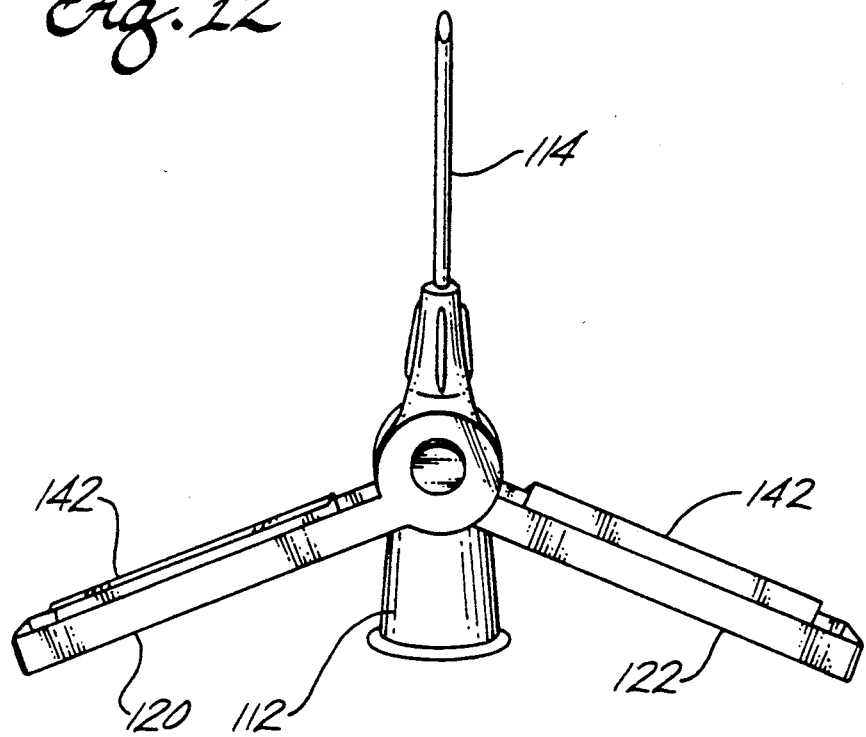
FIG. 12 is a perspective view of the needle and protective cover assembly of FIG. 8 showing the cover fully opened.

As shown in FIG. 12, the first and second halves may be rotated away from each other more than 180°. The magnitude of the maximum angle between the internal surfaces of the first and second halves will be determined in part the outer size and shape of the barrel immediately adjacent the mounting boss 124.

Figure 13:
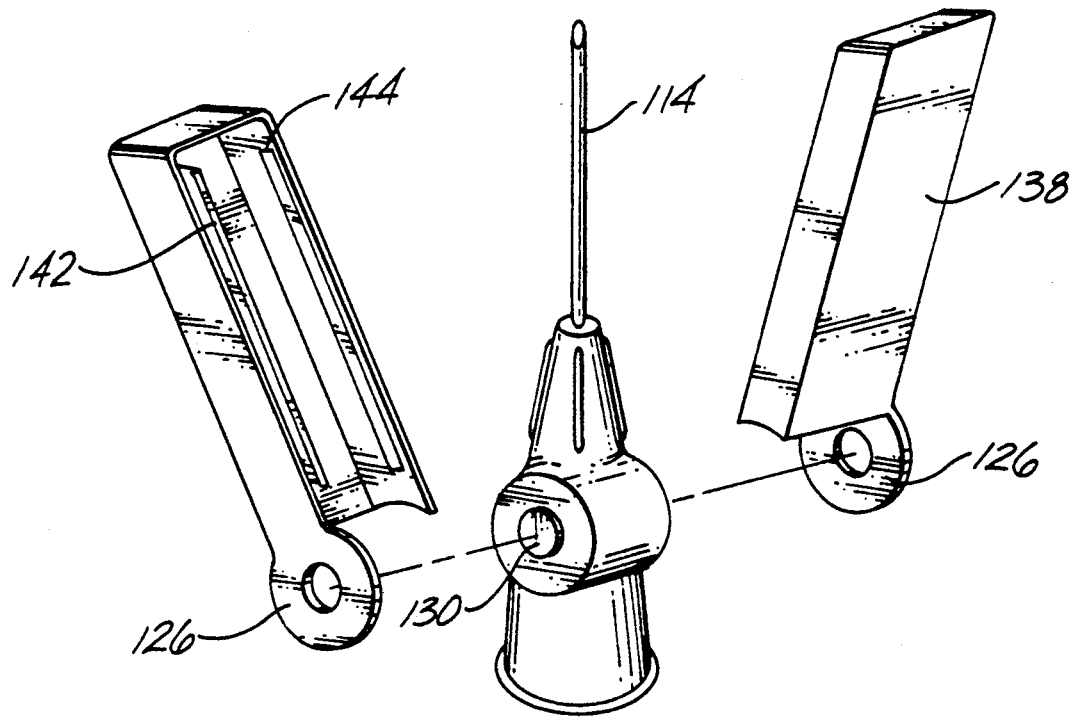
FIG. 13 is a perspective view of the needle and cover assembly of FIG. 8 with the two halves of the cover removed.

FIG. 13 shows more clearly the first and second halves and the mounting boss 124 in a disassembled configuration. As can be seen in the preferred configuration, each half has only one mounting flange.

Once assembled, after manufacture, the needle and cover is preferably sterilized and placed in a sterile, disposable package. The first and second halves are placed closely adjacent one another to protect and cover the needle while leaving the first and second halves unlocked. The halves may be maintained in the closely adjacent position by a cellophane strip around the needle cover or a cellophane cover over the entire assembly. When the needle is ready to be used, the strip or cellophane cover is removed and the needle and cover assembly mounted on the tip of a syringe, for example. To uncover the needle, the user's hand may be placed on the syringe and base of the needle so that the user's thumb and one or more fingers can grasp the base of either half of the needle cover. For example, the thumb and forefinger may grasp the left and right sides 134 and 136, respectively, of the first half of the needle cover. The first half is pulled away from the needle so that it pivots around the first mounting pin 130 to the position shown in FIG. 12. Depending on the amount of frictional engagement between each mounting flange and the corresponding mounting pin, one or both halves of the needle cover may simply fall away from the needle by gravity. The needle is then ready for use.

After the needle has been used, the first and second halves may be pivoted about the base toward each other by placing the thumb and forefinger or two fingers on each side of the base adjacent the back sides of the needle cover. The thumb and forefinger may then be moved along the base pushing the first and second halves so that they pivot toward each other and into the mutually adjacent positions substantially covering the needle. The first and second halves may then be pressed together anywhere along the needle cover, but preferably near the base, to lock the first and second halves together.

With the disclosed needle and cover assembly, the users hands remain behind the needle as the needle is being exposed and recovered. This minimizes the possibility of an accidental needle stick injury. The design also eliminates any need for movement of the user's hands in the direction of the used needle tip. The needle cover is an integral part of the needle so that the cover does not become lost. These benefits are incorporated in the needle cover design to protect the needle and the user both before and after the needle is used. The present design provides a one-way lock for the cover after the needle is used. It also allows easy access to a blood vessel while keeping the cover with the needle. Accidental needle stick is prevented. There is no reason to place the user's fingers near the tip of the needle. Additionally, there is no relative longitudinal movement between the needle and the cover, thereby preventing misalignment or puncture of the needle cover as occurred with removable needle covers. After use, the cover is easily locked around the needle.

Two alternative arrangements for allowing one-handed operation of the needle cover are shown in FIGS. 14 and 15. In the embodiment shown in FIG. 14, the first half 146 is mounted through appropriate flanges on each side of the base 148 on respective mounting pins. The first half includes two mounting flanges which allow the first half to pivot around its mounting pins. The mounting flanges include arcuate portions facing the second half 150 in which are formed gear teeth 152 for engaging corresponding gear teeth 154 on the second half. The second half is pivotally mounted at first and second mounting flanges through respective pivot pins on the base of the needle. The pivot pins for the first and second halves of the needle cover are oriented on the base such that the left, right, and top sides of each half will coincide with those of the other half when the two sides are mutually adjacent, and such that pivoting of the first half about its respective pivot pins will cause simultaneous pivoting of the second half about its corresponding pivot pins, thus allowing one-handed operation of the needle cover.

In the embodiment shown in FIG. 14, the first half may include a ledge 156 mounted on or formed in the back side of the first half to allow the user to place a finger on the ledge and open the first and second halves by pivoting the first half away from the needle. The first and second halves will pivot through respective arcs away from the needle until the needle is sufficiently exposed. After the needle has been used, the user may place a thumb or forefinger against the under side of the ledge and close the first and second halves. The ledge also forms a reference point so that the user knows when the user's fingers reached a point to start closing the first and second halves.

FIG. 15 shows a further gear arrangement for facilitating one-handed operation. The configuration of the second half of the needle cover is substantially the same as that shown in FIG. 14. The first half of the needle cover is also geared as before, but further includes a serrated wheel 158 mounted on or integral with the mounting flange of the first half. In the configuration shown in FIG. 15, the serrated wheel is coupled to the mounting flange of the first half through a splined shaft extending between the serrated wheel and the mounting flange. With this embodiment, one-handed operation can be accomplished.

Although the present invention has been described in details with reference only to the presently preferred embodiments, it will be appreciated by those of ordinary skill in the art that various modifications can be made without departing from the invention. Accordingly, the invention is limited only by the following claims.

What is claimed is:

1. A needle connecting apparatus for connecting a needle to a syringe and for covering the needle for disposal, the apparatus comprising:
   a connector housing including a barrel defining an enclosure;
   first mounting means on the connector housing for mounting the housing to a syringe body;

second mounting means on the connector housing and within the enclosure for mounting a base of a needle to the housing; and a rigid needle cover movably mounted to and guided by the barrel of the connector housing for exposing a needle mounted to the connector housing when in a first position and for covering a needle mounted to the connector housing when in a second position.

2. The apparatus of claim 1 wherein the first mounting means includes a flange for engaging a syringe.

3. The apparatus of claim 1 wherein the second mounting means includes thread elements for engaging a base of a needle.

4. The apparatus of claim 1 wherein the rigid needle cover includes a telescoping needle cover movable along the barrel.

5. The apparatus of claim 4 wherein the telescoping needle cover includes means for locking the needle cover relative to the connector housing when the needle cover is in the second position.

6. The apparatus of claim 5 wherein the needle cover movably engages the barrel through at least one groove and one land in the barrel and the needle cover so that relative movement of the at least one groove and one land allows relative movement of the needle cover and barrel.

7. The apparatus of claim 6 wherein the barrel includes the at least one groove and a stop in the at least one groove and wherein the needle cover includes the at least one land and a locking ridge for engaging the stop on the barrel to lock the needle cover relative to the barrel when in the second position.

8. The apparatus of claim 4 wherein the barrel is a cylindrical barrel includes a cylindrical needle cove wherein the needle cover is slidable longitudinally relative to the cylindrical barrel.

9. The apparatus of claim 8 wherein the needle cover includes an end and wherein the connector housing includes an end such that when the needle cover is in the first position, the end of the needle cover is substantially flush with the end of the connector housing.

10. A needle connecting apparatus for connecting a needle to a syringe and for covering the needle for disposal, the apparatus comprising:

a connector housing including a barrel defining an enclosure;

first mounting means on the connector housing for mounting the housing to a syringe body;

second mounting means on the connector housing and within the barrel for mounting a base of a needle to the housing; and a rigid needle cover telescopically movably engaged with the barrel for exposing a needle mounted to the connector housing when in a first position and for covering a needle mounted to the connector housing when in a second position.

11. The apparatus of claim 10 wherein the rigid needle cover is movably engaged with the barrel through a plurality of lands and grooves.

12. The apparatus of claim 11 further comprising means for locking the needle cover relative to the barrel when the needle cover is in the second position.

13. A needle connecting apparatus for connecting a needle to a syringe and for covering the needle for disposal, the apparatus comprising:

a cylindrical connector housing including a barrel and grooves formed in an outside surface of the barrel extending longitudinally thereof;

a flange element on the connector housing for mounting the connector housing to a syringe body;

thread means on the connector housing for mounting a base of a needle to the housing; and a rigid needle cover including ridges for engaging the grooves in the barrel for allowing the needle cover to move longitudinally relative to the barrel for exposing a needle mounted to the connector housing when in a first position and for covering a needle mounted to the connector housing when in a second position, and further including means for locking the needle cover relative to the barrel when the needle cover is in the second position.

* * * * *